US00PP08706P

United States Patent [19]

Christensen

[11] Patent Number: Plant 8,706

[45] Date of Patent: May 3, 1994

[54] HYBRID TEA ROSE PLANT NAMED 'JACTOU'

[75] Inventor: Jack E. Christensen, Ontario, Calif.

[73] Assignee: Bear Creek Gardens, Inc., Medford, Oreg.

[21] Appl. No.: 17,829

[22] Filed: Feb. 16, 1993

[51] Int. Cl.[5] ..... A01H 5/00

[52] U.S. Cl. ..... Plt./15

[58] Field of Search ..... Plt. 15

*Primary Examiner*—Howard J. Locker

*Attorney, Agent, or Firm*—Klarquist, Sparkman, Campbell, Leigh and Whinston

[57] ABSTRACT

Hybrid tea rose plant having distinctive vigorous upright habit of growth, dark green, disease-resistant foliage, flowers of a pleasant fragrance and deep, stable yellow color, and broad, thick petals.

1 Drawing Sheet

The present invention relates to a new and distinct variety of rose plant of the hybrid tea class which was originated by me by crossing the variety AROcad, U.S. Plant Pat. No. 5,168, with the variety TANsenfrie.

The primary objective of this breeding was to produce a new rose variety having the broad petals and pleasant fragrance of the female parent combined with the rich, deep yellow color of the male parent. The objective was substantially achieved along with other desirable improvements as evidenced by the following unique combination of characteristics which are outstanding in the new variety and which distinguish it from its parents, as well as from all other varieties of which I am aware:

1. Deep, rich, stable yellow color;
2. Broad, thick petals;
3. Vigorous, upright growth habit;
4. Dark green, disease-resistant foliage; and
5. Pleasant fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—AROcad, U.S. Plant Pat. No. 5,168.

*Pollen parent.*—TANsenfrie.

Classification:

*Botanical.*—*Rosa hybrida.*

*Commercial.*—Hybrid tea.

FLOWER

Observations made from specimens grown in a garden in Somis, Calif., from March through August, 1991.

Blooming habit: Recurrent.

Bud:

*Size.*—1½ inches when the petals start to unfurl.

*Form.*—Pointed ovoid.

*Color.*—When sepals first divide, bud color is Yellow Orange Group 15A. When half blown, the upper sides of the petals are Yellow Orange Group 15A; and the lower sides of the petals are Yellow Orange Group 15A.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Apple. Size: Large, broad (⅜×7/16 inches). Surface: Covered in very fine hairs.

*Peduncle.*—Length: Medium (3 to 3½ inches). Surface: Smooth. Color: Medium green. Strength: Stiff, erect.

Bloom:

*Size.*—Large. Average open size is 4½ inches.

*Borne.*—Singly.

*Stems.*—Medium (14 to 18 inches).

*Form.*—When first open: High centered. Permanence: Flattens; outer petals curl back.

*Petalage.*—Number of petals under normal conditions: 25.

*Color.*—The upper side of the petals is Yellow Orange Group 15A. The reverse side of the petals is Yellow Orange Group 15A. The bases of the petals have a small, greenish-white half moon at the point of attachment. The major color on the upper side is Yellow Orange Group 15A.

*Variegations.*—None.

*Discoloration.*—The general tonality at the end of the first day: No change. At the end of the third day, under bright sun and warm conditions there will be some fading on the petal edges to Yellow Orange Group 15B to C.

*Fragrance.*—Moderate.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (4 to 5 days). As a cut flower: Fair (5 to 6 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: White.

*Stigmas.*—Color: Red.

Form: Bush.

Growth: Very vigorous.

Foliage:

*Number of leaflets on normal mid-stem leaves.*—5 or 7.

*Size.*—Large (6 to 7 inches×4 inches).

*Quantity.*—Abundant.

*Color.*—New foliage: Reddish. Old foliage: Dark green, semi-glossy.

Leaflets:

*Shape.*—Pointed oval.

*Texture.*—Upper side: Smooth, semi-glossy.

*Edge.*—Serrated.

*Serration.*—Single.

*Petiole rachis.*—Color: Green.

*Petiol underside.*—Rough with prickles.

*Stipules.*—Long, serrated.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, broad, hooked slightly downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its vigorous upright habit of growth, dark green, disease-resistant foliage, flowers of a pleasant fragrance and deep, stable yellow color, and broad, thick petals.

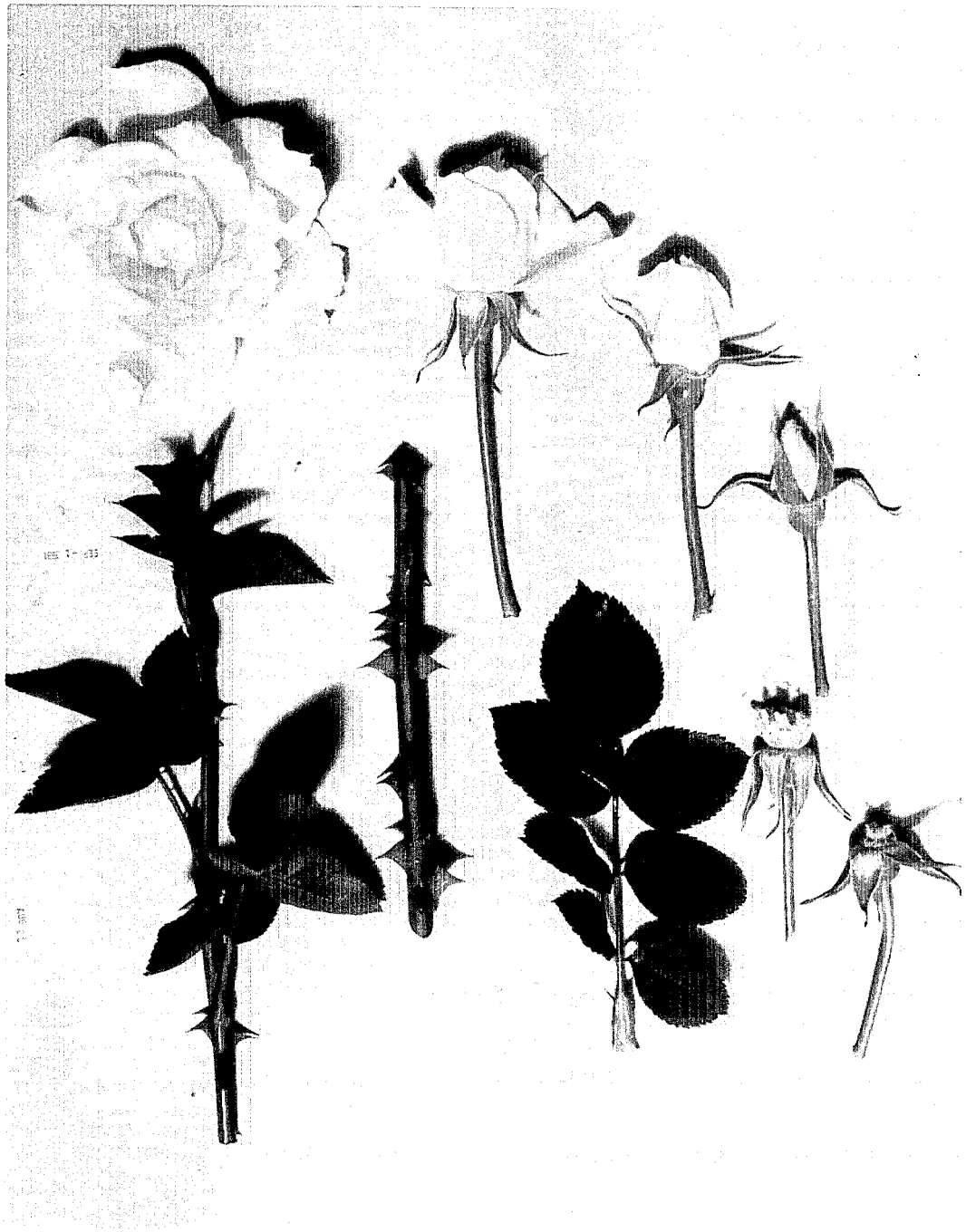

* * * * *